United States Patent
Smal

(10) Patent No.: US 10,694,827 B2
(45) Date of Patent: Jun. 30, 2020

(54) HAIR-REMOVAL SYSTEM

(71) Applicant: BABYLISS FACO SPRL, Wandre (BE)

(72) Inventor: Olivier Smal, Magnee (BE)

(73) Assignee: Conair Corporation, Stamford, CT (US)

( * ) Notice: Subject to any disclaimer, the term of this patent is extended or adjusted under 35 U.S.C. 154(b) by 578 days.

(21) Appl. No.: 15/312,937

(22) PCT Filed: Apr. 30, 2015

(86) PCT No.: PCT/EP2015/059534
§ 371 (c)(1),
(2) Date: Nov. 21, 2016

(87) PCT Pub. No.: WO2015/107229
PCT Pub. Date: Jul. 23, 2015

(65) Prior Publication Data
US 2017/0196336 A1    Jul. 13, 2017

(30) Foreign Application Priority Data

Jul. 29, 2014  (EP) .................................... 14178951

(51) Int. Cl.
*A45D 26/00*    (2006.01)
*A61B 18/20*    (2006.01)
(Continued)

(52) U.S. Cl.
CPC ........... *A45D 26/00* (2013.01); *A45D 44/005* (2013.01); *A61B 18/203* (2013.01);
(Continued)

(58) Field of Classification Search
CPC .................. A45D 26/00; A45D 44/005; A45D 2026/008; H04W 76/14; H04W 4/80; A61B 2018/00988; A61B 2018/00476
See application file for complete search history.

(56) References Cited

U.S. PATENT DOCUMENTS

| 2008/0194928 A1* | 8/2008 | Bandic ................... G16H 15/00 600/306 |
| 2008/0319507 A1* | 12/2008 | Myers .................. A61B 18/203 607/50 |

(Continued)

FOREIGN PATENT DOCUMENTS

| WO | 2012/052976 A1 | 4/2012 |
| WO | 2012052975 A1 | 4/2012 |

(Continued)

*Primary Examiner* — Gary Jackson
*Assistant Examiner* — Sebastian X Lukjan
(74) *Attorney, Agent, or Firm* — Lawrence Cruz, Esq.; Ryan, Mason & Lewis, LLP

(57) ABSTRACT

The present invention is related to a hair-removal system comprising: a mobile phone or tablet computer comprising wireless communication means, a calendar memory with hair-removal session history information and a database comprising treatment time interval and treatment parameters; a light-emitting hair-removal device comprising wireless communication means, said communication means being able to establish interactive communication with the wireless communication means of the mobile phone or tablet computer.

20 Claims, 4 Drawing Sheets

(51) Int. Cl.
*A45D 44/00* (2006.01)
*A61B 18/00* (2006.01)
*H04W 4/80* (2018.01)
*H04W 76/14* (2018.01)

(52) U.S. Cl.
CPC .. *A45D 2026/008* (2013.01); *A45D 2044/007* (2013.01); *A61B 2018/00476* (2013.01); *A61B 2018/00988* (2013.01); *H04W 4/80* (2018.02); *H04W 76/14* (2018.02)

(56) References Cited

U.S. PATENT DOCUMENTS

2012/0010684 A1* 1/2012 Owens ................. A61B 18/203
607/88
2012/0226268 A1* 9/2012 Liu ...................... A61B 18/203
606/9

FOREIGN PATENT DOCUMENTS

WO  WO-2013096572 A1 * 6/2013
WO  WO-2014057481 A2 * 4/2014

\* cited by examiner

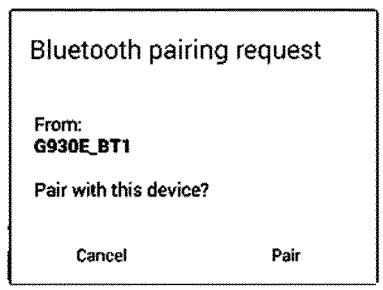
Fig.4a
Fig.4b
Fig.4c
Fig.4d

HAIR-REMOVAL SYSTEM

FIELD OF THE INVENTION

The present invention is related to the cosmetic treatment of human skin, and in particular to a hair-removal system associating an electromagnetic energy emitting device for hair removal and a wireless communication with a mobile phone or tablet computer for the management of skin treatment.

BACKGROUND AND STATE OF THE ART

Hair-removal devices are well known in the art. The former mechanical devices with epilator discs for temporary hair removal are progressively replaced by electromagnetic energy emitting devices such as laser or pulsed-light epilators performing medium and long term epilation.

Originally, electromagnetic energy emitting devices such as laser or pulsed-light epilators were only used in clinics by educated professionals managing the possible security issues of such devices. The latest trend in the market of skin-treatment devices is miniaturization and recently, home-use devices have been commercialized moving skin treatments, and in particular light-epilation treatments, from a professional context into the home environment, where non-professional users operate in privacy. Since inappropriate handling of home-use devices can entail injuring like skin irritation, the safety aspect represents a real challenge for the manufacturers.

The private user is confronted with at least four parameters, namely the location and the intensity of the skin treatment as well as the associated frequency and interval. Additional parameters to be considered are the history of the skin exposure to UV light, the type of skin and the age of the applicant.

In this context, it was necessary to invent a system associating an epilation device with a management support for all those parameters allowing the private user to set up a safe and adequate treatment program for the epilation of various parts of his/her body.

Mobile phones, in particular the so called "smart phones" and "tablets", the variety of screen sizes making the differentiation between "smart phones", "tablets" of various sizes and "portable computer" difficult, are nowadays much more than just communication tools. A continuously-growing number of available applications (camera, GPS, agenda, etc.) and wireless communication (Bluetooth) with a series of manageable devices are now possible.

The wireless communication capacity of these devices therefore represents a major opportunity to achieve tailor-made systems to manage skin-treatment devices, and in particular electromagnetic energy emitting devices for hair-removal systems.

WO 2014/057481 A2 discloses a system for personal skin procedures based on the interaction of a camera-equipped portable computer with an electromagnetic energy emitting device, the extracted information from a taken picture of the skin being the basis for a computer analysis leading to a specific treatment of the skin.

WO 2012/052976 A1 and WO 2012/052975 A1 disclose methods and devices for monitoring the use of a pulsed-light skin-treatment device in order to avoid fraudulent use of said device regarding the number of flashes and the types of treatments actually performed. The described methods do not allow personal planning such as treatment frequency, adaptation to individual user's skin types and relevant processing areas.

AIMS OF THE INVENTION

The present invention aims to provide a hair-removal system comprising a light emitting based epilator having wireless communication means associated to a skin-treatment management system via a smart phone or a tablet computer.

SUMMARY OF THE INVENTION

The present invention is related to a hair-removal system comprising:
 a mobile phone or tablet computer comprising wireless communication means, a calendar memory with hair-removal session history information and a database comprising treatment-time interval and treatment parameters;
 a light-emitting hair-removal device comprising wireless communication means, said communication means being able to establish interactive communication with the wireless communication means of the mobile phone or tablet computer.

Preferred embodiments of the present invention disclose at least one or a suitable combination of the following features:
 the light-emitting hair-removal device comprises a pulsed-light source, producing in use light pulses at selectable energy fluence and repetition rate;
 said pulsed-light source is able to produce light pulses at selectable energy fluence comprised between 1 and 10 $J/cm^2$, preferably between 2 and 8 $J/cm^2$, and most preferably between 2 and 6 $J/cm^2$;
 said pulsed-light source is able to produce light pulses at selectable repetition rate comprised between 1 and 5 s and preferably between 1.5 and 3.5 s;
 the pulsed-light source produces pulses having duration comprised between 0.1 and 10 ms, preferably between 0.5 and 2 ms, and most preferably between 0.6 and 0.9 ms;
 said hair-removal session history comprises at least the date of the last session, the pulse fluence of the last session and the number of pulses of the last session on the body part treated.

A second aspect of the invention is related to a method for hair-removal, using the system of the invention, comprising the steps of:
 retrieving the last session information on a specific body part stored in a calendar memory of the phone or tablet computer;
 determining time interval between the last session date and the current date;
 comparing said determined time interval with the treatment time interval stored in the database, and if the determined time interval is larger than the preconized treatment time interval, indicate on the phone or tablet screen the authorization of a new epilation session;
 sending, if a new epilation session on said specific body part is authorized, the phone or tablet computer treatment parameters for said body part to the light-emitting hair-removal device;
 performing the hair-removal session with the light-emitting hair-removal device on the specific body part;

sending back the session parameters, emitted from the light-emitting hair-removal device, to the phone or tablet and storing a new session history in a calendar for the body part treated.

Preferably, the method of the invention comprises the additional step of determining the skin status prior to the treatment, said skin status being related to at least one of the following information: sun exposure, skin irritation, use of cosmetic or therapeutic cream, and adapting the treatment accordingly.

Advantageously, said method is applied recursively as a background task on said phone or tablet computer, a reminder being shown on the screen as soon as the time interval condition is fulfilled.

The present invention is also related to a light-emitting hair-removal device comprising wireless communication means, said communication means being able to establish a two-ways communication link with a mobile phone or tablet computer.

FIGURES

FIGS. 4a to 4h represent various snapshots of the screen appearing to the user.

KEY

Figure 1:
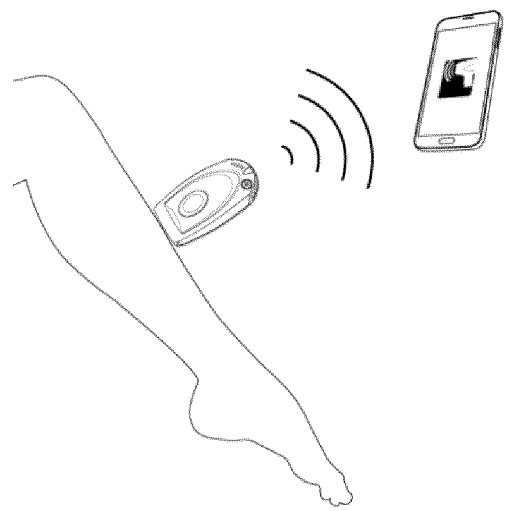
FIG. 1 represents an example of the hair-removal system according to the invention.
Figure 2:
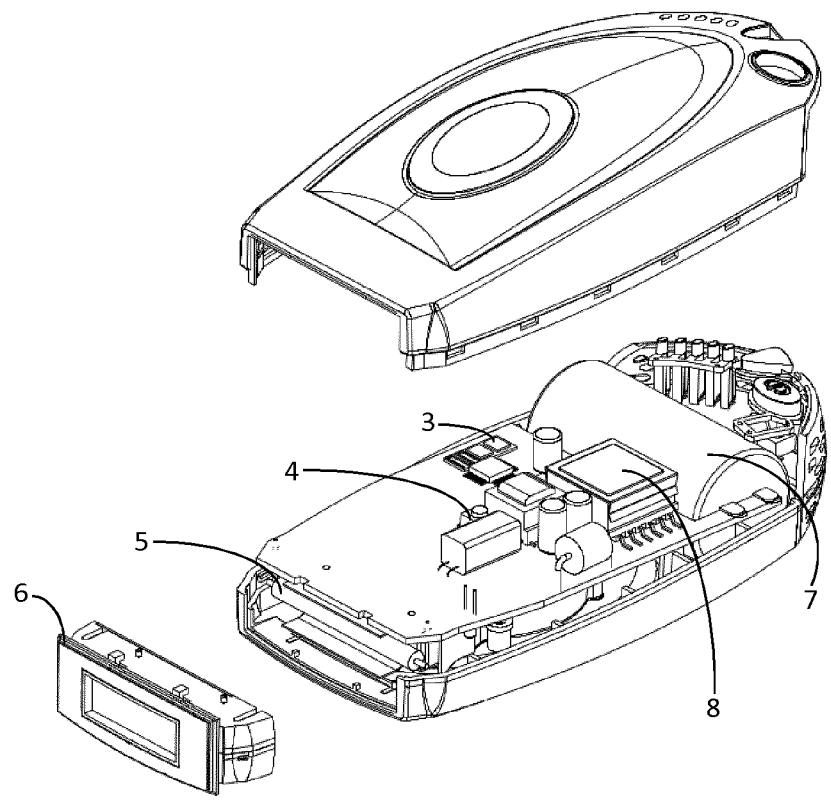
FIG. 2 represents an example of the light-emitting epilation device according to the invention.
Figure 3:
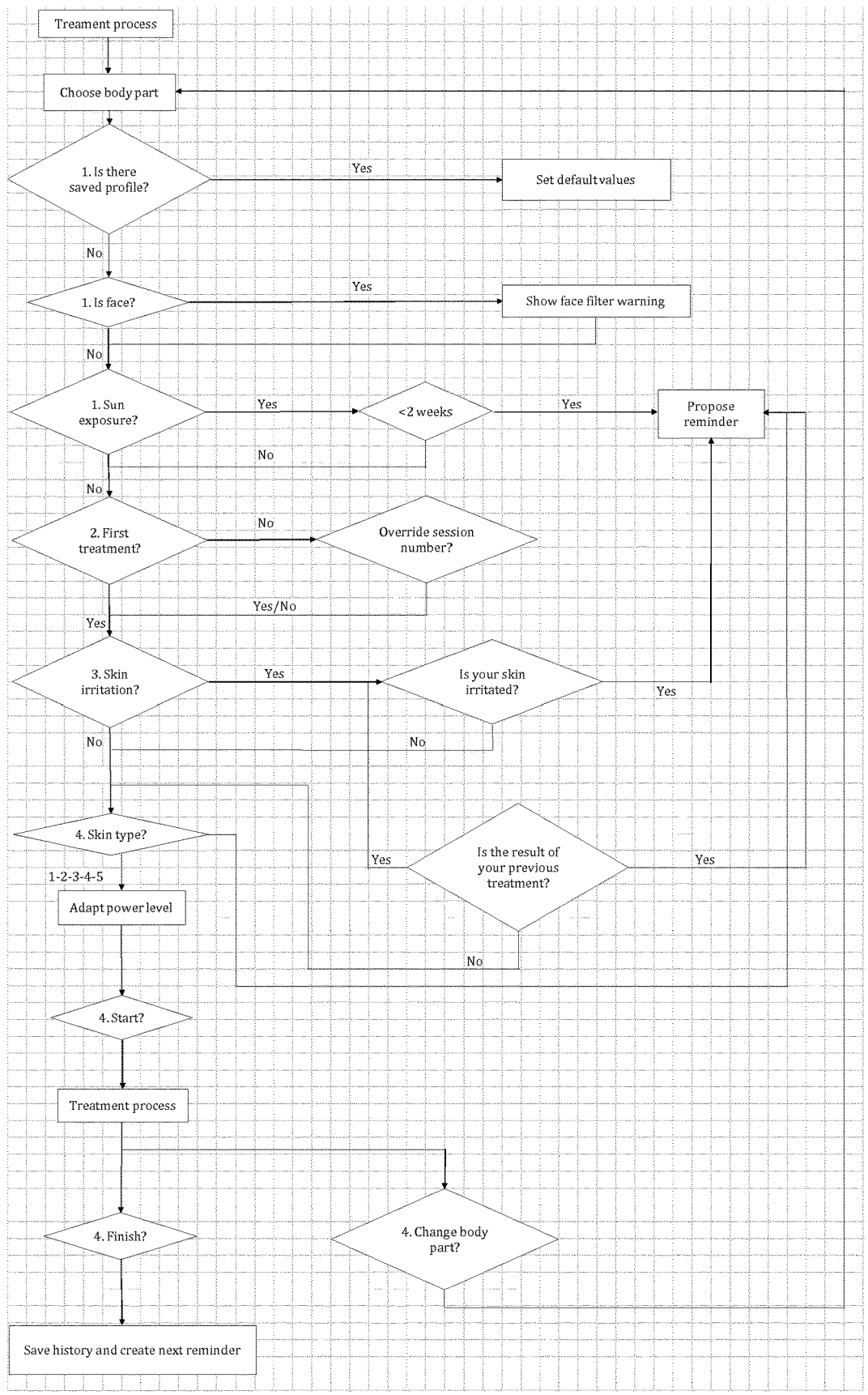
FIG. 3 represents an organigram of an application implementing the method according to the invention.
Figure 4E:
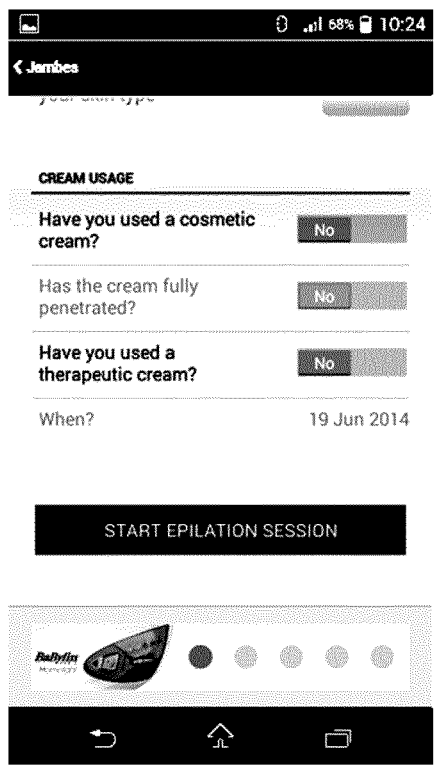
Figure 4F:
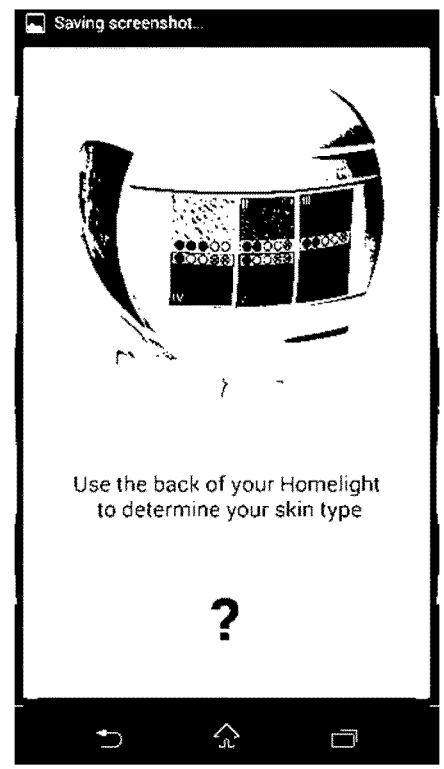
Figure 4G:
Figure 4H:
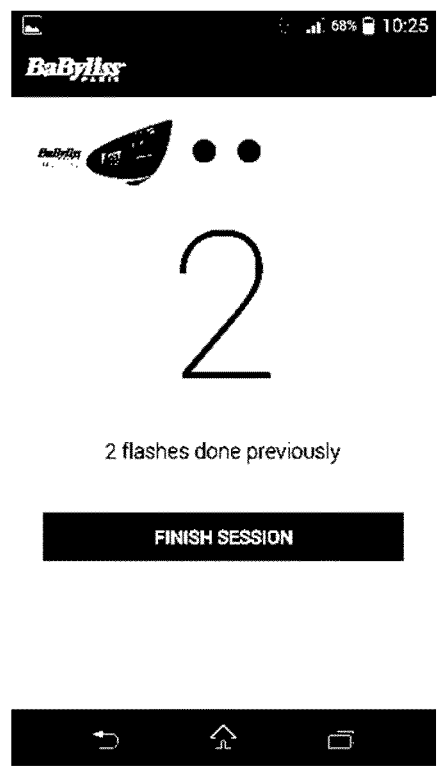

1. Pulsed light source epilation device
2. Mobile phone or tablet computer
3. Wireless communication means (Bluetooth)
4. Trigger button
5. Flashtube
6. Capacitive sensor for skin detection
7. Capacitor
8. Transformer

DETAILED DESCRIPTION OF THE INVENTION

The present invention is related to a hair-removal system. The hair removal is performed by a pulsed-light source 1 such as a flash lamp for example. The technology is called IPL (for Intense Pulsed Light). The energy level of the flash can be adapted on the device itself or via communication means over mobile phone or tablet computer.

Preferably, the light source can be operated at five energy levels with the following exemplative parameters:

The duration of the pulse at 50% intensity, between 0.5 ms and 0.9 ms;
The repetition rate of the pulse is about 1.6 s at level 1 and 3.5 s at level 5;
The fluence is split in 5 levels as followed:

|  | Level 1 | Level 2 | Level 3 | Level 4 | Level 5 |
|---|---|---|---|---|---|
| Fluence (J/cm$^2$) | 2.0 | 3.0 | 3.5 | 4.0 | 4.5 |

Wavelengths between 550 and 1200 nm;
Window size: 300 mm$^2$;

A face filter can be added (wavelengths between 600 and 1200 nm and window size is 150 mm$^2$).

Advantageously, the hair-removal device 1 comprises a capacitive sensor 6 to detect the skin contact.

The hair-removal device 1, part of the system of the invention, also comprises wireless communication means 3 such as a Bluetooth chip for providing a two-ways link with a smartphone or a tablet computer 2. Such communication means are used to establish communication between the hair-removal device 1 and an application running on the smart phone 2 in order to exchange true treatment data (energy fluence, number of pulses, etc.) to be used in the next epilation session.

The purpose of the Bluetooth chip 3 is to communicate with a smartphone 2. An application (App) on the smartphone 2 helps the user to choose the correct setting corresponding to his/her skin and provides assistance during the hair-removal session.

The App advantageously comprises an automatic session calendar with session history. Preferably, the calendar also provides a reminder function. The automatic calendar feature helps the user controlling his/her hair-removal sessions. Hair-removal sessions have to follow a precise schedule. Therefore, the App is programmed to advise the user when the next hair-removal session is appropriate. If the user is not available for hair-removal session when the reminder sends an alert, it is possible to reprogram a new reminder.

Preferably, default body parts are selectable and custom body parts can be editable, the automatic calendar comprising specific information for each body part, so that the App independently controls the schedule for each body part and allows its independent treatment.

Advantageously, the App comprises a personal questionnaire to select the correct energy level.

A history is kept for each body part. In the history, the user can see all the different sessions performed on the selected body part. For each session, the energy level, the date and the number of light pulses is memorized.

The user can choose his/her body part in a default list (e.g. leg, underarm, bikini line . . . ). The user can also add a custom part. Custom parts can also be deleted by the user.

In order to define the correct level of energy to be applied, questions are asked to the user. Preferred questions and corresponding treatment adaptation are:

Sun exposure: if the user has been exposed to the sun less than 15 days ago, a treatment is not recommended;
First treatment: the user treats the body part for the first time with the App. It is still possible that the user already made some treatments without the App. It is therefore possible to introduce the number of session already done without the App in order to correctly follow the hair-removal schedule for the selected body part;
Skin irritation now or during last session: if the user has skin irritation, a treatment is not recommended. The energy level is adapted according to the irritation level perceived during the last treatment;
User's skin photo type: the skin colour has to be selected to define the energy level range to be applied;
Use of therapeutic or cosmetic cream: in case of use of therapeutic cream, a treatment is not recommended. A new treatment is only recommended when the cream is fully penetrated.

After the questionnaire has been completed and validated, the session screen appears. On this screen, the following data appears:
Body part, Selected energy level,
Number of flashes during the current session,
Number of flashes performed during the previous session.
Security functions are also implemented in the system. In that case, a warning is given to the user, for example in case of:
Selection of a not-recommended level of energy,
Request of a hair-removal session before the due date,
Sun exposure less than 15 days ago,
Use of therapeutic cream less than 7 days ago,
Use of cosmetic cream not fully penetrated,
Changes of the energy level during the treatment,
Advantageously, the communication protocol is a two-channel communication for both the device and the smartphone or tablet computer:
The smartphone sends information each time it is needed;
The device is listening all the time and is sending its report regularly.
Preferred transmitted data are:
The smartphone is able to change the energy level of the epilation device;
The device send the performed number of flashes to the smartphone, the energy level and some information about defective parts when the user modifies the energy level on the device, the value is also communicated to the smartphone.
The transmitted report lists the following parameter:
Up-link communication (hair-removal device to smartphone)

| Life | | | | Voltage-Fan-Temperature-Level | | | | | |
|---|---|---|---|---|---|---|---|---|---|
| Byte 1 | Byte 2 | Byte 3 | Byte 4 | Byte 5 | | | | | |
| Low byte send first | | | | 7 Reserved | 6 | 5 V | 4 F | 3 T | 2 1 0 Level |

Failure report on App:
Life exceeds 130 k flash; the App displays a warning message: "End of life of the product";
Bit_5 of byte_5 (V) is at 0 for 10 times consecutively. App displays a warning message: "Charging Failure";
Bit_4 of byte_5 (F) is at 0. App displays warning message: "Fan Failure";
Bit_3 of byte_5 (T) is at 0. App displays warning message: "Temperature too high";
Down-link communication (Smartphone to IPL)

| | Level Byte1 | |
|---|---|---|
| 2 | 1 Level 0 to 4 | 0 |

The invention claimed is:
1. Hair-removal system, comprising:
a mobile phone or tablet computer comprising a first wireless communication system, a calendar memory and a database comprising treatment-time interval and treatment parameters; and
a light-emitting hair-removal device comprising:
a pulsed light source configured to produce light pulses at one or more selectable energy fluence and repetition rates; and
a second wireless communication system, the second wireless communication system being configured to establish interactive communication with the first wireless communication system of the mobile phone or tablet computer;
wherein the calendar memory of the mobile phone or tablet computer is configured to store session data in the database, the session data related to hair-removal treatment sessions of the hair-removal device for one or more select body parts, the data comprising at least one of a treatment date, an energy level, and a light pulse frequency and duration;
wherein the mobile phone or the tablet computer includes programming configured to determine the treatment time interval and treatment parameters for the one or more select body parts based at least in part on input received from an operator;
wherein the hair removal device is configured to transmit data to the mobile phone or tablet computer, the data relating to an operational status of the hair removal device; and
wherein the programming of the mobile phone or tablet computer is further configured to:
retrieve prior treatment session data on a given body part of the one or more select body parts stored in the calendar memory of the mobile phone or tablet computer;
determine an actual time interval between a last session date of the prior session and a current date;
compare the actual time interval with the treatment time interval stored in the database, and if the actual time interval is larger than the treatment time interval, indicate on a screen of the mobile phone or tablet computer authorization of a new epilation session;
send, if a new treatment session on the given body part is authorized, the mobile phone or tablet computer treatment parameters for the given body part to the light-emitting hair-removal device; and
receive back session parameters of the new treatment session, emitted from the light-emitting hair-removal device, to the mobile phone or tablet computer and store a new session data corresponding to the new treatment session in the calendar memory for the given body part.
2. System according to claim 1, wherein the pulsed-light source is configured to produce light pulses at a selectable energy fluence between 1 and 10 j/cm$^2$.
3. System according to claim 2, wherein the pulsed-light source is configured to produce light pulses at a selectable repetition rate between 1 and 5 s.
4. System according to claim 3, wherein the pulsed-light source is configured to produce pulses having a duration between 0.1 and 10 ms.
5. System according to claim 1, wherein the hair-removal session history comprises at least the date of the last session, the energy fluence of the last session and the number of pulses of the last session on the given body part.
6. Hair-removal system, which comprises:
a mobile phone or tablet computer comprising a first wireless communication system, a calendar memory and a database comprising treatment-time interval and treatment parameters; and
a light-emitting hair-removal device comprising:
a pulsed light source configured to produce light pulses at one or more selectable energy fluence and repetition rates; and a second wireless communication system, the second wireless communication system being configured to establish interactive communication with the first wireless communication system of the mobile phone or tablet computer;

wherein the mobile phone or the tablet computer includes programming configured to:

retrieve prior treatment session data on a given body part stored in the calendar memory of the mobile phone or tablet computer;

determine an actual time interval between a last session date of the prior session and a current date;

compare the actual time interval with the treatment time interval stored in the database, and if the actual time interval is larger than the treatment time interval, indicate on a screen of the mobile phone or tablet computer authorization of a new epilation session;

send, if a new treatment session on the given body part is authorized, the mobile phone or tablet computer treatment parameters for the given body part to the light-emitting hair-removal device; and receive back session parameters of the new treatment session, emitted from the light-emitting hair-removal device, to the mobile phone or tablet computer and store a new session data corresponding to the new treatment session in the calendar memory for the given body part.

7. System according to claim 6, wherein the programming of the mobile phone or tablet computer is configured to:

determine the skin status prior to the new treatment session, the skin status being related to at least one of the following information: sun exposure, skin irritation, use of cosmetic or therapeutic cream.

8. System according to claim 1, wherein the programming of the mobile phone or tablet computer is configured to change an energy level of the pulsed light source of the hair-removal device.

9. System according to claim 1, wherein the operational status includes information relative to one or more defective parts of the hair-removal device.

10. System according to claim 1, the operational status includes an end of use of the hair-removal device based on a predetermined parameter of use of the hair-removal device.

11. System according to claim 10, wherein the predetermined parameter of use includes a total number of light pulses of the pulsed light source of the hair-removal device.

12. System according to claim 1, wherein the operational status includes a determination of a charging failure of the hair-removal device.

13. System according to claim 1, wherein the operational status includes a determination of a fan failure of the hair-removal device.

14. System according to claim 1, wherein the operational status includes a determination of a high temperature of the pulsed light source of the hair-removal device.

15. System according to claim 1, wherein the mobile phone or tablet computer includes a screen, the screen configured to display the treatment time interval and treatment parameters for the given body part.

16. System according to claim 1, wherein the programming includes an application stored on the mobile phone or tablet computer.

17. A computer program product comprising a non-transitory computer readable storage medium for implementation in a mobile phone or tablet computer and having programming instructions that when executed by a processor is configured to:

receive instructions based on operator input and develop a treatment protocol comprising treatment-time interval and treatment parameters for a remote hair-removal device to facilitate removal of hair from one or more body parts;

receive session treatment data from the hair-removal device and store the session treatment data in a calendar memory of the mobile phone or tablet computer;

receive operational data from the hair-removal device relative to an operational status of the hair-removal apparatus; and a wireless communication system configured to establish interactive communication with a wireless communication system of the hair-removal device;

wherein the processor is further configured to:

retrieve prior treatment session data on a given body part of the one or more body parts stored in the calendar memory of the mobile phone or tablet computer;

determine an actual time interval between a last session date of the prior session and a current date;

compare the actual time interval with the treatment time interval stored in the database, and if the actual time interval is larger than the treatment time interval, indicate on a screen of the mobile phone or tablet computer authorization of a new epilation session;

send, if a new treatment session on the given body part is authorized, the mobile phone or tablet computer treatment parameters for the given body part to the hair-removal device; and receive back session parameters of the new treatment session, emitted from the hair-removal device, to the mobile phone or tablet computer and store a new session data corresponding to the new treatment session in the calendar memory for the given body part.

18. The computer program product according to claim 17, wherein the operational status includes at least one of:

a total number of light pulses of a pulsed light source of the hair-removal device;

a determination of a charging failure of the hair-removal device;

a determination of a fan failure of the hair-removal device; or a determination of a high temperature of the pulsed light source of the hair-removal device.

19. System according to claim 1, wherein the programming of the mobile phone or tablet computer is further configured to:

determine the skin status prior to the new treatment session, the skin status being related to at least one of the following information: sun exposure, skin irritation, use of cosmetic or therapeutic cream.

20. The computer program product according to claim 17, wherein the processor is further configured to:

determine the skin status prior to the new treatment session, the skin status being related to at least one of the following information: sun exposure, skin irritation, use of cosmetic or therapeutic cream.

* * * * *